(12) United States Patent
Ilowite

(10) Patent No.: US 8,658,619 B2
(45) Date of Patent: Feb. 25, 2014

(54) METHODS OF TREATING SUBCLINICAL SUN DAMAGE

(76) Inventor: Robert K. Ilowite, Hillsborough, NJ (US)

( * ) Notice: Subject to any disclaimer, the term of this patent is extended or adjusted under 35 U.S.C. 154(b) by 168 days.

(21) Appl. No.: 13/008,539

(22) Filed: Jan. 18, 2011

(65) Prior Publication Data

US 2011/0301115 A1 Dec. 8, 2011

Related U.S. Application Data

(60) Provisional application No. 61/352,200, filed on Jun. 7, 2010.

(51) Int. Cl.
*A01N 43/04* (2006.01)
*A61K 31/70* (2006.01)

(52) U.S. Cl.
USPC ................ 514/50; 514/43; 514/49; 514/51

(58) Field of Classification Search
None
See application file for complete search history.

(56) References Cited

U.S. PATENT DOCUMENTS

| | | | |
|---|---|---|---|
| 2,885,396 A | 5/1959 | Heidelberger et al. | |
| 7,521,459 B2 | 4/2009 | Baumann et al. | |
| 2004/0180919 A1 | 9/2004 | Miller et al. | |

OTHER PUBLICATIONS

Askew et al. International Journal of Dermatology (2009), vol. 48, pp. 453-463.*
Loven et al. Clinical Therapeutics (2002), vol. 24, pp. 990-1000.*
"Carac Cream", *DERMIK* Nov. 2006, 4 pgs.
EFUDEX (fluorouracil) Topical Solutions and Cream, *ICN Pharmaceuticals, Inc.* Dec. 2000, 2 pgs.
"Increase in Leisure Time", http://www.cottontown.org/page.cfm?pageid=398&language=eng Jan. 28, 2009, 2 pgs.
Amini, MD, Sadegh et al., "Nonsurgical Innovations in the Treatment of Nonmelanoma Skin Cancer", *The Journal of Clinical and Aesthetic Dermatology*, vol. 3, No. 6 Jun. 2010, 16 pgs.
Brunk, Doug, "Imiquimond Tied to Immune Activation for AKs", *Skin & Allergy News*, vol. 36, Issue 12 http://www.skinandallergynews.com/article/PHS003763370570855/fulltext?search_article . . . Dec. 2005, 2 pgs.
Chen, MD, John G. et al., "Cost of nonmelanoma Skin Cancer Treatment in the United States", *Dermatologic Surgery*, vol. 27, Issue 12 http://www3.interscience.wiley.com/journal/118991314/abstract?CRETRY=1&SRETRY=0 Dec. 20, 2001, 1 pg.
ClinicalTrials.gov "The VA Keratinocyte Carcinoma Chemoprevention Trial" Updated Feb. 18, 2009.
ClinicalTrials.gov "NCT00847912 Skin Cancer Prevention (VAKCCT)" First Received: Feb. 18, 2009 Last Updated: Jun. 8, 2010.
Kim, MD, Andrew D. et al., "Optimizing Management of Actinic Keratosis and Photodamaged Skin: Utilizing a Stepwise Approach", *Therapeutics for the Clinician*, vol. 84 Sep. 2009, 169-175 pgs.

* cited by examiner

*Primary Examiner* — Patrick Lewis
(74) *Attorney, Agent, or Firm* — Servilla Whitney LLC; Karen M. Whitney

(57) ABSTRACT

Provided are methods of treating subclinical sun damage and of inducing a chemocytotoxic response in skin. Methods of treating subclinical sun damage include the steps of: topically administering to skin of a patient a composition comprising a chemocytotoxic agent in an amount effective to induce erythema, scaling, crusting, or combinations thereof and resolve at least a portion of the subclinical sun damage, where the skin has a condition of no clinical sign of sun damage and the patient was not previously treated for actinic keratosis or nonmelanoma skin cancer. The chemocytotoxic agent can comprise a fluorinated pyrimidine antimetabolite such as 5-fluorouracil (FU), 5-fluorouridine (FUR), 5-fluorouridine-5'-monophosphate (FUMP), 5-fluorodeoxyuridine (FUdR), 5-fluorodeoxyuridine-5'-monophosphate (FdUMP), or combinations thereof.

19 Claims, 4 Drawing Sheets
(4 of 4 Drawing Sheet(s) Filed in Color)

METHODS OF TREATING SUBCLINICAL SUN DAMAGE

CROSS-REFERENCE TO RELATED APPLICATIONS

This application claims priority under 35 U.S.C. §119(e) to U.S. Patent Application Ser. No. 61/352,200, filed Jun. 7, 2010, which is hereby incorporated by reference in its entirety.

TECHNICAL FIELD

The present invention relates to methods of treating subclinical sun damage and of inducing a chemocytotoxic response through application of a chemocytotoxic agent. Specific such agents comprise a fluorinated pyrimidine antimetabolite, for example, 5-fluorouracil.

BACKGROUND

Since the 19th century, there has been an increase in leisure time with much of that time being spent outdoors. As such, many baby boomers and young adults have had moderate to extensive unprotected sun exposure. Generally, the results of cumulative sun exposure are not clinically apparent for many decades after exposure. The first clinical signs of sun damage often are actinic keratoses (AKs) and sometimes nonmelanoma skin cancers. The treatment of AKs and nonmelanoma skin cancers can cause substantial morbidity and scarring, as well as cost millions of dollars annually. Various topical compositions for AKs and nonmelanoma skin cancers are indicated by the FDA for treatment. Clinicians use, for example, 5-fluorouracil (5-FU) cream, a fluorinated pyrimidine antimetabolite, for the topical treatment of solar or actinic keratoses (AKs). 5-FU is a chemocytotoxic agent, which means that it induces cell death upon uptake by receptive cells, such as cells that are actinically damaged. Rather than delaying treatment until the onset of clinically apparent sun damage, there is a need to reduce morbidity and scarring by prophylactically treating sun damage. That is, there is a need to treat subclinical sun damage.

SUMMARY

Provided are methods of treating subclinical sun damage and of inducing a chemocytotoxic response in skin. Methods of treating subclinical sun damage include the steps of: topically administering to skin of a patient a composition comprising a chemocytotoxic agent in an amount effective to induce erythema, scaling, crusting, or combinations thereof and resolve at least a portion of the subclinical sun damage, where the skin has a condition of no clinical sign of sun damage and the patient was not previously treated for actinic keratosis or nonmelanoma skin cancer.

A detailed method of treating subclinical sun damage includes the steps of: topically administering to skin in need thereof a composition consisting essentially of 5-fluorouracil and one or more pharmaceutically acceptable carriers or excipients in an amount effective to induce erythema, scaling, crusting, or combinations thereof and resolve at least a portion of the subclinical sun damage, where the skin has a condition of no clinical sign of sun damage, no previous actinic keratosis, and no previous nonmelanoma skin cancer.

Also provided are methods of inducing a chemocytotoxic response in skin having a condition of no clinical sign of sun damage, no previous actinic keratoses, and no previous nonmelanoma skin cancer, the methods comprising: topically administering to the skin having the condition an effective amount of a composition comprising a chemocytotoxic agent during a cycle of therapy that is in the range of two to four weeks; and observing the skin for the response; wherein the composition is administered once or twice daily during the cycle of therapy, which is repeated at least once on a substantially annual basis.

BRIEF DESCRIPTION OF THE DRAWINGS

The figures depict participants before and after treatment. The patent or application file contains at least one drawing executed in color. Copies of this patent or patent application publication with color drawing(s) will be provided by the Office upon request and payment of the necessary fee.

DETAILED DESCRIPTION

Figure 1A:
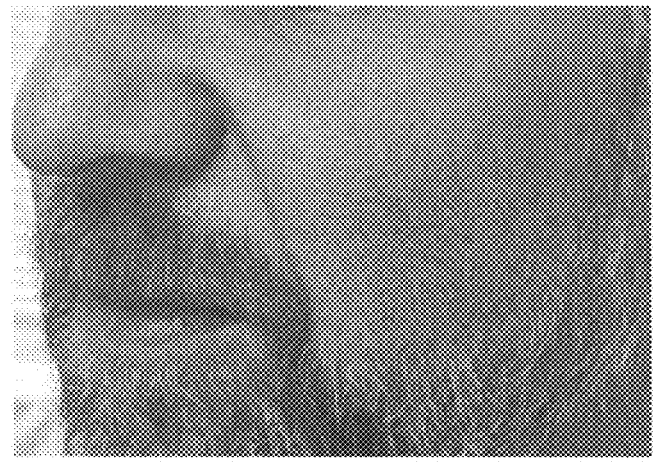
FIG. 1A is a color photograph of a participant before treatment.

Currently, 5-fluorouracil (5-FU) cream is indicated for the treatment of actinic keratoses (AKs). 5-FU cream is not currently indicated for the treatment of unblemished skin, that is, skin with no clinically apparent AKs or nonmelanoma skin cancer. During treatment of AKs with 5-FU cream, subclinical sun damage often will become clinically apparent. Actinically damaged cells grow and divide more rapidly and take up 5-FU at a greater rate than undamaged healthy skin cells. Without intending to be bound by theory, it is believed that once absorbed, 5-FU interferes with the synthesis of DNA, and to a lesser extent RNA, which thereby causes cell death that appears clinically as erythema, scaling, and/or ulceration.

What has not been shown until the present invention is that 5-FU can invoke a response indicative of treating subclinical sun damage for skin that was not previously subjected to treatment for AKs or nonmelanoma cancer. It is unexpected that otherwise seemingly undamaged skin can benefit from an agent that historically was only used for apparent damage. The present invention shows that for a variety of unblemished skin types, 5-FU can detect subclinical sun damage and resolve at least a portion of it. Moreover, substantially annual application of 5-FU leads to continued elimination of subclinical sun damage accumulated throughout the year.

Before describing several exemplary embodiments of the invention, it is to be understood that the invention is not limited to the details of construction or process steps set forth in the following description. The invention is capable of other embodiments and of being practiced or being carried out in various ways.

Provided are methods of treating subclinical sun damage and of inducing a chemocytotoxic response in skin. Methods of treating subclinical sun damage include the steps of: topically administering to skin of a patient a composition comprising a chemocytotoxic agent in an amount effective to induce erythema, scaling, crusting, or combinations thereof and resolve at least a portion of the subclinical sun damage, where the skin has a condition of no clinical sign of sun damage and the patient was not previously treated for actinic keratosis or nonmelanoma skin cancer.

In one or more embodiments, the chemocytotoxic agent comprises a fluorinated pyrimidine antimetabolite. Exemplary fluorinated pyrimidine antimetabolites include: 5-fluorouracil (FU), 5-fluorouridine (FUR), 5-fluorouridine-5'-monophosphate (FUMP), 5-fluorodeoxyuridine (FUdR), 5-fluorodeoxyuridine-5'-monophosphate (FdUMP), or combinations thereof. In a detailed embodiment, the chemocytotoxic agent comprises 5-fluorouracil.

The composition can comprise the chemocytotoxic agent in an amount in the range of 0.25 to 10% by weight, or 0.5 to 5% by weight, or even or 2.5 to 5% by weight. The composition containing the chemocytotoxic agent can include one or more pharmaceutically acceptable carriers or excipients. Exemplary carriers can be, but not limited to propylene glycol, tris(hydroxymethyl)aminomethane, hydroxypropylcellulose, parabens (methyl and/or propyl) and disodium edentate. Other inactive ingredients can include: carbomer 940, dimethicone. glycerin, methyl gluceth-20, methyl methacrylate/glycol dimethacrylate crosspolymer, octyl hydroxy stearate, polyethylene glycol 400, polysorbate 80, purified water, sorbitan monooleate, stearic acid, and trolamine.

One embodiment provides that the composition is applied in a dosage of 0.01 to 1 mg/cm$^2$.

As to administration frequency, the composition can be administered in a cycle of therapy that is in the range of two to four weeks. In a detailed embodiment, the composition is administered once or twice daily during the cycle of therapy. Another embodiment provides that the cycle of therapy is repeated at least once on a substantially annual basis. By substantially annual basis it is meant that administration can take place at about yearly intervals, where, for example, no fewer than 325 days and no more than 400 days have passed between treatments.

A detailed method of treating subclinical sun damage includes the steps of: topically administering to skin in need thereof a composition consisting essentially of 5-fluorouracil and one or more pharmaceutically acceptable carriers or excipients in an amount effective to induce erythema, scaling, crusting, or combinations thereof and resolve at least a portion of the subclinical sun damage, where the skin has a condition of no clinical sign of sun damage, no previous actinic keratosis, and no previous nonmelanoma skin cancer. In one embodiment, the composition comprises 5-fluorouracil in an amount in the range of 0.25 to 10% by weight, or in a preferred range of 0.5 to 5% by weight.

Also provided are methods of inducing a chemocytotoxic response in skin having a condition of no clinical sign of sun damage, no previous actinic keratoses, and no previous nonmelanoma skin cancer, the methods comprising: topically administering to the skin having the condition an effective amount of a composition comprising a chemocytotoxic agent during a cycle of therapy that is in the range of two to four weeks; and observing the skin for the response; wherein the composition is administered once or twice daily during the cycle of therapy, which is repeated at least once on a substantially annual basis.

A study was undertaken to determine if participants with no clinically apparent AKs had subclinical sun damage that could be identified with the application of 5-FU cream. In this study, 5-fluorouracil (5-FU) cream was applied to the faces of 23 participants (14 female, 9 male) between the ages of 35 and 55 years with no medical history of AKs or nonmelanoma skin cancers to determine if subclinical lesions could be identified and treated. Participants were instructed to apply the composition to their entire face. One of the participants did not return for observation, but the results showed that 100% (22/22) of participants in this study who returned for observation had a positive reaction to 5-FU cream, indicating that they had subclinical sun damage that became clinically apparent.

Fitzpatrick Skin Type is defined as follows in Table 1.

TABLE 1

| Classification | Response to Ultraviolet Rays |
| --- | --- |
| I | Never tans, always burns |
| II | Tans with difficulty, usually burns |
| III | Average tanning, sometimes burns |
| IV | Easily tans, rarely burns |

The present invention shows that for a variety of unblemished skin types, 5-FU can detect subclinical sun damage and resolve at least a portion of it. In Table 2, data regarding gender, skin type, sunburn history, medication, days of treatment, and observations are provided. Medication is defined as "E" for Efudex cream (5.0% 5-FU, twice daily for approximately 2 weeks) or "C" for Carac cream (0.5% 5-FU, once daily for approximately 2 weeks).

TABLE 2

| Patient ID | M/F | Fitzpatrick Skin Type | Sunburn History | Medication | Days of treatment | Observations |
| --- | --- | --- | --- | --- | --- | --- |
| 1 | F | IV | Occasional | E | 14 | + |
| 2 | F | III | Occasional | E | 14 | + |
| 3 | F | II | Many | E | 14 | ++ |
| 4 | F | II | Many | C | 21 | +++ |
| 5 | M | IV | Occasional | E | 14 | ++ |
| 6 | F | II | Occasional | E | 14 | ++ |
| 7 | F | II | Many | C | 21 | ++ |
| 8 | M | III | Many | C | 14 or so | +++ |
| 9 | M | IV | Many | C | 14 | +++ |
| 10 | F | III | Many | C | 7 | + |
| 11 | M | II | Many | C | 14 | + |
| 12 | M | III | Occasional | C | 14 | ++ |
| 13 | F | II | Occasional | C | 14 | ++ |
| 14 | F | III | Many | C | 14 or so | − |
| 15 | M | III | Occasional | E | 13 | +++ |
| 16 | M | I | Many | E | 15 | ++ |
| 17 | M | I | Many | C | 14 | +++ |
| 18 | F | III | Occasional | C | 14 | + or so* |
| 19 | F | II | Occasional | C | 21 | ++ or so* |
| 20 | F | III | Occasional | C | 14 | +++ |
| 21 | F | III | Occasional | E | 13 | +++ |
| 22 | F | III | Occasional | E | 14 | ++ |
| 23 | M | II | Many | E | 24 | +++ |

*observations occurred multiple days after treatment had been stopped.

The observations have the general meanings as provided in Table 3, where amount of response includes visual observation of erythema, scaling, and/or crusting.

TABLE 3

| Observation | Response |
| --- | --- |
| + | Mild Erythema |
| ++ | Erythema |
| +++ | Moderate Erythema |

Figure 1B:
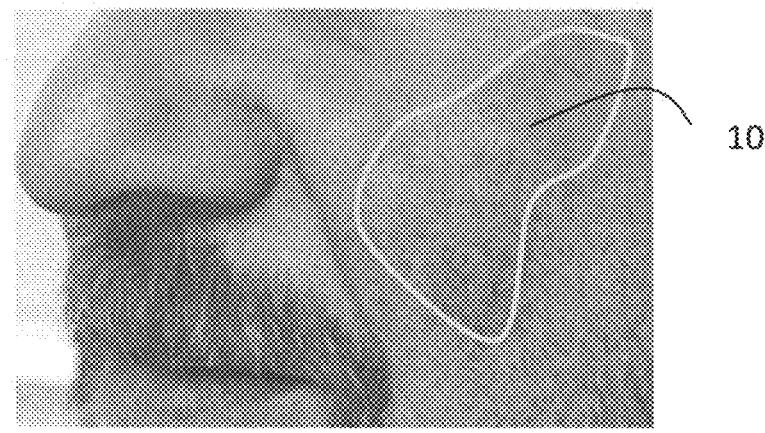
FIG. 1B is a color photograph of this participant who showed a reaction of very mild erythema after fourteen days of treatment.
Figure 2A:
FIG. 2A is a color photograph of a participant before treatment.
Figure 2B:
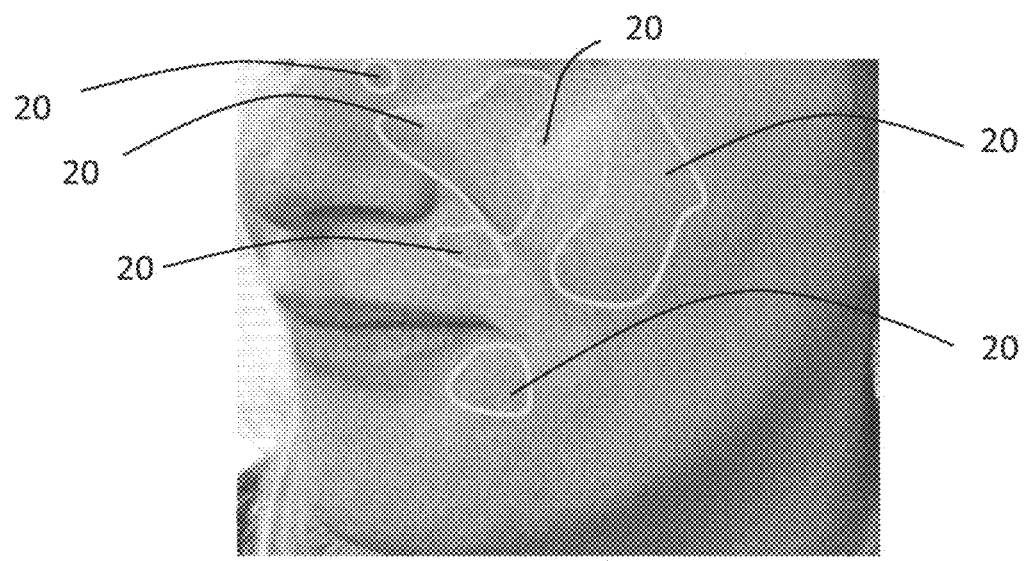
FIG. 2B is a color photograph of this participant who showed a reaction of erythema after seven days of treatment.
Figure 3A:
FIG. 3A is a color photograph of a participant before treatment.
Figure 3B:
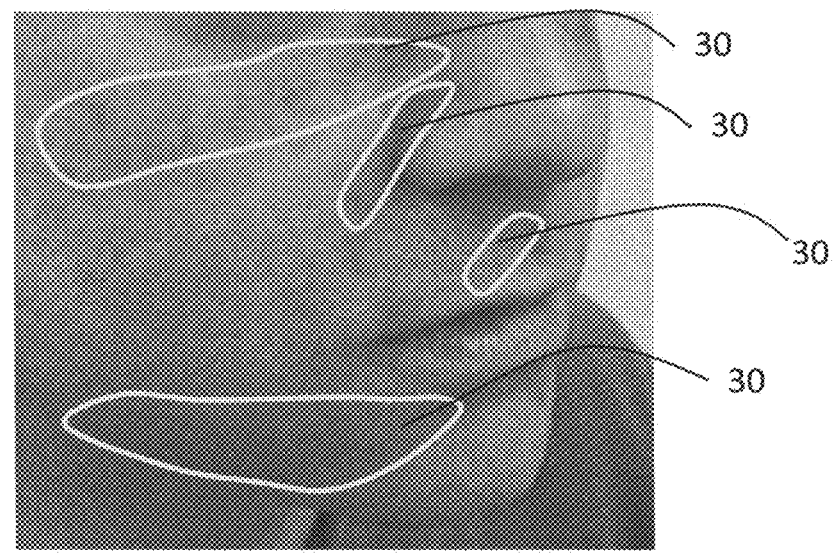
FIG. 3B is a color photograph of this participant who showed a reaction of moderate erythema after fourteen days of treatment.

With reference to the figures and Table 3, FIG. 1B depicts a reaction of mild erythema after fourteen days of treatment corresponding to "+". FIG. 1B shows an area of mild erythema 10 that was not present in the untreated skin of FIG. 1A. FIG. 2 depicts a reaction of erythema after seven days of treatment corresponding to "++". Multiple areas of erythema 20 are shown in FIG. 2B where there were no areas of red in FIG. 2A. FIG. 3B depicts a reaction of moderate erythema after fourteen days of treatment corresponding to "+++". FIG. 3B shows areas of crusting 30, including an intense reaction on the chin, in accordance with moderate erythema, where FIG. 3A shows no areas of redness.

Figure 4A:
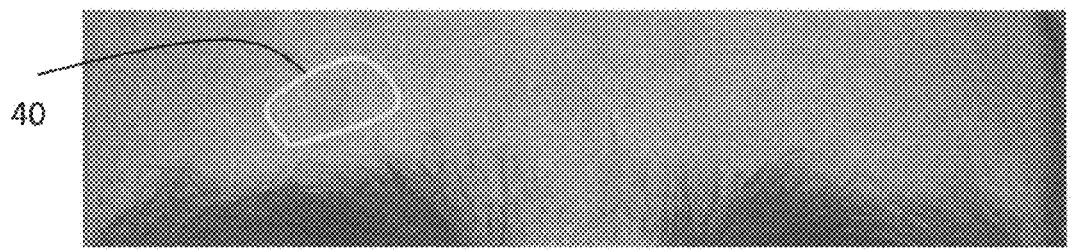
FIG. 4A is a color photograph of a participant before treatment.
Figure 4B:
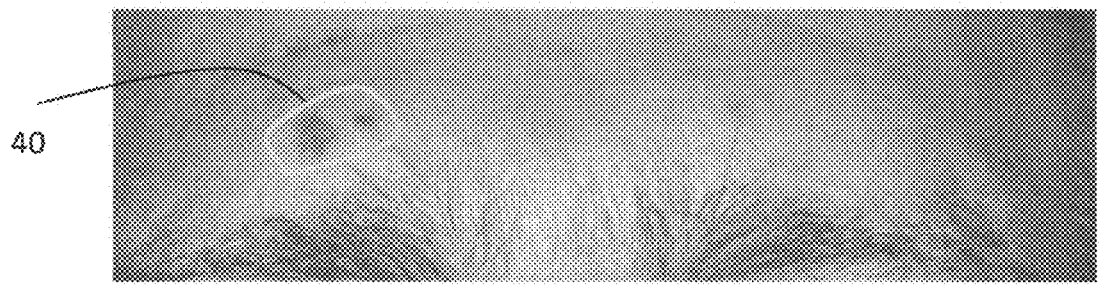
FIG. 4B is a color photograph of this participant who showed a reaction after treatment.
Figure 4C:
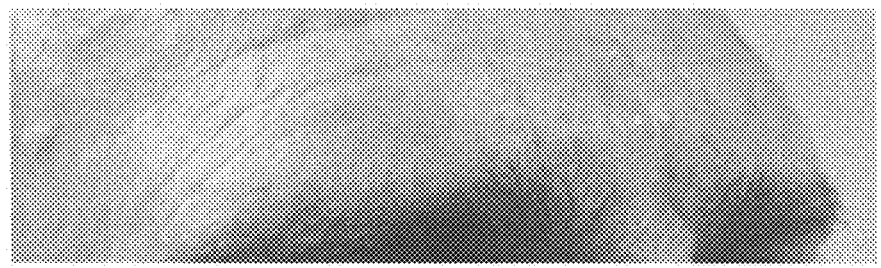
FIG. 4C is a color photograph of this participant during a subsequent follow-up treatment.

In order to assess the scope of original treatment, one patient received further treatments over a substantially annual basis. In Table 4, treatment #, days since last treatment, and observations are provided. Over the course of follow-up treatment, it was observed that a response of mild erythema to 5-FU was seen each time after the first treatment that showed erythema. From this, it was concluded that all of the subclinical sun damage treated most likely resolved during each cycle of therapy. Subsequent milder reactions appear to have treated new subclinical sun damage or possible recurrent sun damage. It was also noted that what appeared to be a mere freckle 40 on the participant's forehead during the first treatment as shown in FIG. 4A, ended up crusting and scaling 40 during follow-up treatment # 1 as shown in FIG. 4B. The freckle also resolved itself after follow-up treatment #1. During follow-up treatment #2, FIG. 4C, there was no sign of the freckle. That is, where there may not have been a response during an earlier treatment, a subsequent treatment invoked a response. Moreover, responses to successive treatments, if any, were not as severe as the initial response. Follow-up treatments # 3 and #4 showed no signs of the freckle, nor was there any erythema. It is also concluded that annual treatment aids in preventing actinic keratoses from forming as well as eliminates any new sun damage.

TABLE 4

| Patient ID | Follow-up # | Days since last treatment | Medication Assignment | Days of treatment | Observations |
| --- | --- | --- | --- | --- | --- |
| 12 | 1 | +399 days | C | 14 | + |
| 12 | 2 | +344 days | C | 14 | + |
| 12 | 3 | +364 days | C | 14 | + |
| 12 | 4 | +373 days | C | 14 | + |

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of treating subclinical sun damage, the method comprising:
    topically administering to unblemished skin of a patient which has no clinically apparent actinic keratosis or nonmelanoma skin cancer, and was not previously treated for actinic keratosis or nonmelanoma skin cancer, a composition comprising a chemocytotoxic agent in an amount effective to induce erythema, scaling, crusting, or combinations thereof;
    wherein an erythema, scaling and/or crusting response is indicative of treatment of the subclinical sun damage.

2. The method of claim 1, wherein the chemocytotoxic agent comprises a fluorinated pyrimidine antimetabolite.

3. The method of claim 2, wherein the fluorinated pyrimidine antimetabolite comprises: 5-fluorouracil (FU), 5-fluorouridine (FUR), 5-fluorouridine-5'-monophosphate (FUMP), 5-fluorodeoxyuridine (FUdR), 5-fluorodeoxyuridine-5'-monophosphate (FdUMP), or combinations thereof.

4. The method of claim 3, wherein the chemocytotoxic agent comprises 5-fluorouracil.

5. The method of claim 1, wherein the composition is applied in a dosage in a range of 0.01 to 1 mg/cm$^2$.

6. The method of claim 1, wherein the composition is administered in a cycle of therapy that in the range of two to four weeks.

7. The method of claim 1, wherein the composition is administered once or twice daily during the cycle of therapy.

8. The method of claim 1, wherein the cycle of therapy is repeated at least once on a substantially annual basis.

9. The method of claim 1, wherein the composition further comprises one or more pharmaceutically acceptable carriers or excipients.

10. A method of treating subclinical sun damage, the method comprising:
    topically administering to unblemished skin having no previous actinic keratosis or nonmelanoma skin cancer a composition consisting essentially of 5-fluorouracil and one or more pharmaceutically acceptable carriers or excipients in an amount effective to induce erythema, scaling, crusting, or combinations thereof;
    wherein an erythema, scaling and/or crusting response is indicative of treatment of the subclinical sun damage.

11. The method of claim 10, wherein the composition is administered in a cycle of therapy that is in the range of two to four weeks.

12. The method of claim 10, wherein the composition is administered once or twice daily during the cycle of therapy.

13. The method of claim 10, wherein the cycle of therapy is repeated at least once on a substantially annual basis.

14. The method of claim 10, wherein the composition comprises 5-fluorouracil in an amount in the range of 0.25 to 10% by weight.

15. The method of claim 14, wherein the composition comprises the 5-fluorouracil in an amount in the range of 0.5 to 5% by weight.

16. A method of inducing a chemocytotoxic response in skin having subclinical sun damage, no previous actinic keratoses, and no previous nonmelanoma skin cancer, the method comprising:
   topically administering to the skin having the condition an effective amount of a composition comprising a chemocytotoxic agent during a cycle of therapy that is in the range of two to four weeks; and
   observing the skin for the response;
   wherein the composition is administered once or twice daily during the cycle of therapy, which is repeated at least once on a substantially annual basis.

17. The method of claim 16, wherein the chemocytotoxic agent comprises a fluorinated pyrimidine antimetabolite.

18. The method of claim 16, wherein the fluorinated pyrimidine antimetabolite comprises 5-fluorouracil.

19. A method of preventing actinic keratosis comprising topically administering to unblemished skin an amount of a chemocytotoxic agent effective to induce death of actinically damaged cells in the unblemished skin, wherein death of the actinically damaged cells is visible as erythema, scaling and/or crusting.

* * * * *